(12) United States Patent
Smith et al.

(10) Patent No.: US 11,090,500 B2
(45) Date of Patent: Aug. 17, 2021

(54) FIXATION DEVICE AND METHODS FOR AN IMPLANTABLE MEDICAL DEVICE

(71) Applicant: Advanced Bionics AG, Staefa (CH)

(72) Inventors: James George Elcoate Smith, Santa Clarita, CA (US); Sung Jin Lee, Valencia, CA (US); Mark B. Downing, Valencia, CA (US)

(73) Assignee: Advanced Bionics AG, Staefa (CH)

( * ) Notice: Subject to any disclaimer, the term of this patent is extended or adjusted under 35 U.S.C. 154(b) by 127 days.

(21) Appl. No.: 16/147,419

(22) Filed: Sep. 28, 2018

(65) Prior Publication Data

US 2020/0101305 A1 Apr. 2, 2020

(51) Int. Cl.
*A61N 1/375* (2006.01)
*A61N 1/36* (2006.01)
*A61N 1/05* (2006.01)

(52) U.S. Cl.
CPC ....... *A61N 1/37518* (2017.08); *A61N 1/0541* (2013.01); *A61N 1/36038* (2017.08)

(58) Field of Classification Search
CPC .............. A61N 1/37518; A61N 1/0541; A61N 1/36038; A61N 1/36036; A61N 1/375
See application file for complete search history.

(56) References Cited

U.S. PATENT DOCUMENTS

| 5,545,191 A * | 8/1996 | Mann ................. A61N 1/37229 607/57 |
| 8,626,309 B1 | 1/2014 | Alshemari |
| 2006/0116743 A1 | 6/2006 | Gibson et al. |
| 2009/0099658 A1 * | 4/2009 | Dalton .................. A61N 1/375 623/11.11 |
| 2015/0246234 A1 | 9/2015 | Hazard et al. |
| 2016/0302011 A1 * | 10/2016 | Olsen .................. H04R 25/606 |

FOREIGN PATENT DOCUMENTS

WO  WO-2010/083554  7/2010

* cited by examiner

*Primary Examiner* — Joseph M Dietrich
(74) *Attorney, Agent, or Firm* — ALG Intellectual Property, LLC (57) ABSTRACT

A fixation device for use with an implantable medical device includes a body member comprising a contact surface shaped to conform to an outer surface of the implantable medical device, an adhesion element provided on a contact surface of the body member and configured to attach the body member to the outer surface of the implantable medical device, and an anchor member extending from the body member and having a hole for securing the fixation device to a human body while the body member is attached to the outer surface of the implantable medical device.

20 Claims, 12 Drawing Sheets

FIXATION DEVICE AND METHODS FOR AN IMPLANTABLE MEDICAL DEVICE

BACKGROUND INFORMATION

Maintaining the position of an implantable medical device, such as a cochlear implant, within a recipient is often desired, both during and after a surgical procedure in which the medical device is implanted within the recipient. After the medical device has been implanted, the recipient's tissue around the implant site generally heals over time (typically about six to twelve months), thus securing the medical device in place. However, a surgeon may be concerned that an implanted medical device might migrate within a recipient during the surgical procedure to implant the medical device, or that the medical device might migrate before the recipient's tissue around the implant site has healed enough to secure the medical device in place. Hence, it would be desirable for the surgeon to be able to selectively secure the medical device within the recipient. Unfortunately, some implantable medical devices are not designed in a way that allows a surgeon to conveniently and safely secure them within a recipient.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Fixation devices and methods for securing an implantable medical device within a recipient are described herein. For example, a fixation device for use with an implantable medical device may include a body member having a contact surface shaped to conform to an outer surface of the implantable medical device, an adhesion element provided on a contact surface of the body member and configured to attach the body member to the outer surface of the implantable medical device, and an anchor member extending from the body member and having a hole for securing the fixation device to the recipient while the body member is attached to the surface of the implantable medical device. In some examples, the adhesion element may be a gecko adhesive, which may be formed integrally with the body member. Additionally or alternatively, the adhesion element may be an adhesive film coated on the contact surface of the body member.

The fixation device can be selectively attached to an implantable medical device and used to secure the implantable medical device within a recipient of the implantable medical device. To illustrate, prior to or during a surgical procedure in which a cochlear implant assembly is implanted within a recipient, a surgeon may attach a fixation device as described herein to the cochlear implant assembly to prevent migration of the cochlear implant assembly after implantation of the cochlear implant assembly within the recipient. To this end, the surgeon may remove a peel-off wrapper covering an adhesion element on the fixation device and attach the fixation device to an outer surface of the cochlear implant assembly. The surgeon may then position the cochlear implant assembly, with the attached fixation device, within the recipient (e.g., within a periosteal pocket formed within the recipient) and secure the fixation device within the recipient's body. For example, the surgeon may insert a fastener (e.g., a bone screw or a suture) through the hole of the anchor member and secure the fastener to a bone or tissue within the recipient. After implantation, the fixation device securely holds the cochlear implant assembly in place while the recipient's tissue heals around the implant site.

Various benefits and advantages may be realized by the fixation device and methods described herein. For example, the adhesion element on the contact surface of the fixation device is strong enough to securely hold the implantable medical device in place while the recipient's tissue around the implant site heals. Additionally, the adhesion element allows the fixation device to be attached to the implantable medical device without any other mechanical fastening means, such as a snap-on fit, screw, or other fastener. Accordingly, there are no crevices or special features formed in the outer surface of the implantable medical device or the fixation device where undesirable biofilms can grow, which can cause complications such as infection and implant rejection. Additionally, the fixation devices and methods described herein may be used with legacy implantable medical devices without modification or redesign of the legacy implantable medical devices.

The fixation devices and methods described herein may be used with any suitable implantable medical device. For example, the implantable medical device may be a cochlear implant assembly included in a cochlear implant system. As such, an exemplary cochlear implant system will now be described. The described exemplary cochlear implant system is illustrative and not limiting.

Figure 1:
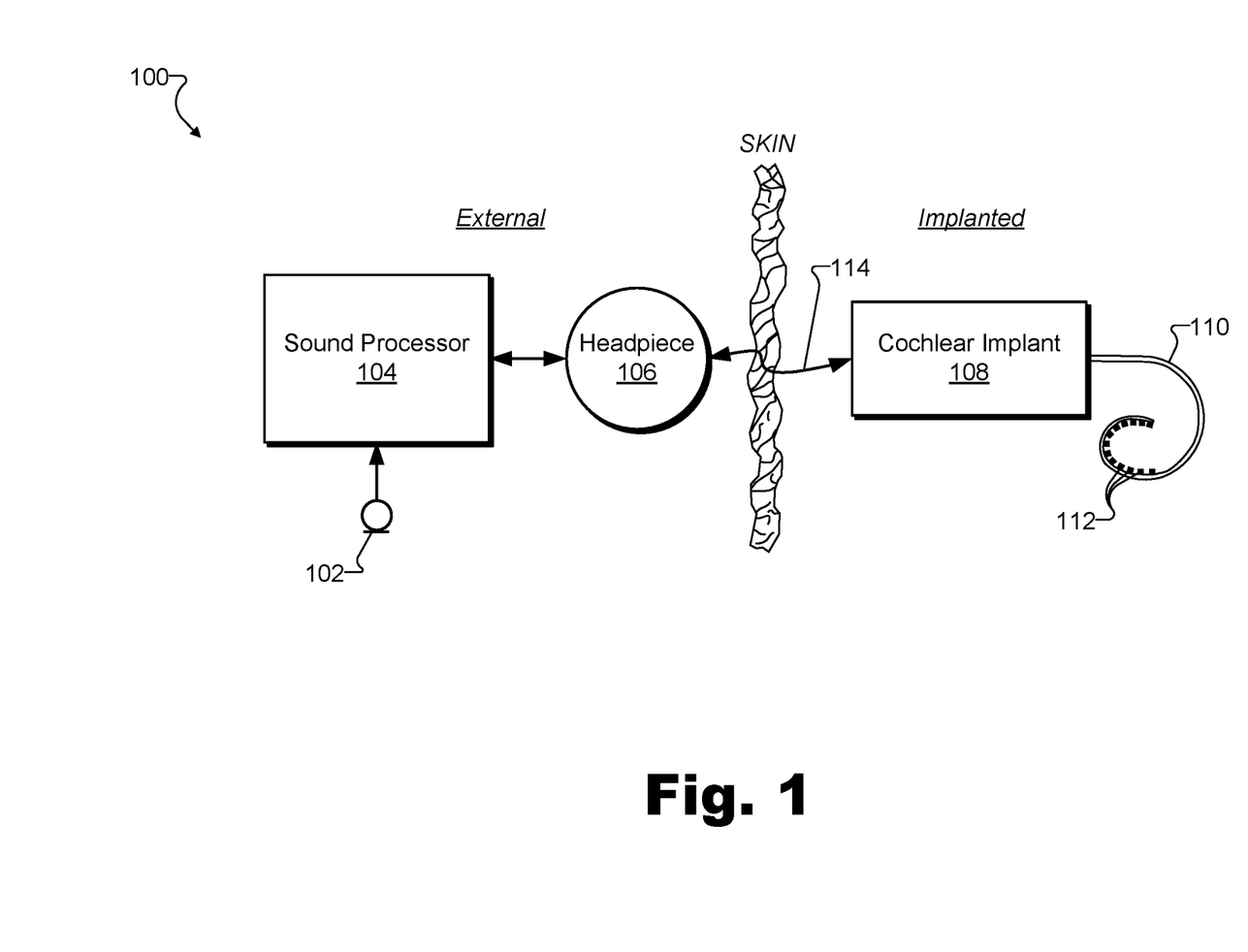
FIG. 1 illustrates an exemplary cochlear implant system according to principles described herein.

FIG. 1 shows an exemplary cochlear implant system 100. As shown, cochlear implant system 100 may include various components configured to be located external to a cochlear implant recipient including, but not limited to, a microphone 102, a sound processor 104, and a headpiece 106. Cochlear implant system 100 may further include various components configured to be implanted within the recipient including, but not limited to, a cochlear implant 108 (also referred to as an implantable cochlear stimulator) and a cochlear lead 110 (also referred to as an intracochlear electrode array) with a plurality of electrodes 112 disposed thereon. In certain examples, additional or alternative components may be included within cochlear implant system 100 as may serve a particular implementation. The components shown in FIG. 1 will now be described in more detail.

Microphone 102 may be configured to detect audio signals presented to the recipient. Microphone 102 may be implemented in any suitable manner. For example, microphone 102 may include a microphone such as a T-MIC™ microphone from Advanced Bionics. Microphone 102 may be associated with a particular ear of the recipient such as by being located in a vicinity of the particular ear (e.g., within the concha of the ear near the entrance to the ear canal). In some examples, microphone 102 may be held within the concha of the ear near the entrance of the ear canal by a boom or stalk that is attached to an ear hook configured to be selectively attached to sound processor 104. Additionally or alternatively, microphone 102 may be implemented by one or more microphones disposed within headpiece 106, one or more microphones disposed within sound processor 104, one or more beam-forming microphones, and/or any other suitable microphone or microphones as may serve a particular implementation.

Sound processor 104 (i.e., one or more components included within sound processor 104) may be configured to direct cochlear implant 108 to generate and apply electrical stimulation (also referred to herein as "stimulation current") representative of one or more audio signals (e.g., one or more audio signals detected by microphone 102, input by way of an auxiliary audio input port, etc.) to one or more stimulation sites associated with an auditory pathway (e.g., the auditory nerve) of the recipient. Exemplary stimulation sites include, but are not limited to, one or more locations within the cochlea, the cochlear nucleus, the inferior colliculus, and/or any other nuclei in the auditory pathway. While, for the sake of simplicity, electrical stimulation will be described herein as being applied to one or both of the cochleae of a recipient, it will be understood that stimulation current may also be applied to other suitable nuclei in the auditory pathway. To this end, sound processor 104 may process the one or more audio signals in accordance with a selected sound processing strategy or program to generate appropriate stimulation parameters for controlling cochlear implant 108. Sound processor 104 may include or be implemented by a behind-the-ear ("BTE") unit, a body worn device, and/or any other sound processing unit as may serve a particular implementation. For example, sound processor 104 may be implemented by an electro-acoustic stimulation ("EAS") sound processor included in an EAS system configured to provide electrical and acoustic stimulation to a recipient.

In some examples, sound processor 104 may wirelessly transmit stimulation parameters (e.g., in the form of data words included in a forward telemetry sequence) and/or power signals to cochlear implant 108 by way of a wireless communication link 114 between headpiece 106 and cochlear implant 108. It will be understood that communication link 114 may include a bidirectional communication link and/or one or more dedicated unidirectional communication links. In some examples, sound processor 104 may execute and operate in accordance with a sound processing program that has been loaded into memory contained within sound processor 104.

Headpiece 106 may be communicatively coupled to sound processor 104 and may include an external antenna (e.g., a coil and/or one or more wireless communication components) configured to facilitate selective wireless coupling of sound processor 104 to cochlear implant 108. Headpiece 106 may additionally or alternatively be used to selectively and wirelessly couple any other external device to cochlear implant 108. To this end, headpiece 106 may be configured to be affixed to the recipient's head and positioned such that the external antenna housed within headpiece 106 is communicatively coupled to a corresponding implantable antenna (which may also be implemented by a coil and/or one or more wireless communication components) included within or otherwise associated with cochlear implant 108. In this manner, stimulation parameters and/or power signals may be wirelessly transmitted between sound processor 104 and cochlear implant 108 via communication link 114.

Cochlear implant 108 may include any type of implantable device and/or hardware that may be used in association with the devices, systems, and methods described herein. For example, cochlear implant 108 may be implemented by an implantable cochlear stimulator. In some alternative implementations, cochlear implant 108 may include a brainstem implant and/or any other type of active implant or auditory prosthesis that may be implanted within a recipient and configured to provide, by way of cochlear lead 110, stimulation to one or more stimulation sites located along an auditory pathway of a recipient. Additionally, cochlear implant 108 may include an implantable antenna configured to facilitate wireless communication with headpiece 106 via communication link 114.

In some examples, cochlear implant 108 may be configured to generate stimulation current representative of an audio signal processed by sound processor 104 (e.g., an audio signal detected by microphone 102) in accordance with one or more stimulation parameters transmitted thereto by sound processor 104. Cochlear implant 108 may be further configured to provide the stimulation current to cochlear lead 110, which may be configured to apply electrical stimulation representative of the audio signal to one or more stimulation sites within the recipient via one or more electrodes 112 disposed along cochlear lead 110 (e.g., by way of one or more stimulation channels formed by electrodes 112). In some examples, cochlear implant 108 may include a plurality of independent current sources each associated with a channel defined by one or more of electrodes 112. In this manner, different stimulation current levels may be applied to multiple stimulation sites simultaneously (also referred to as "concurrently") by way of multiple electrodes 112.

Cochlear implant 108 may be included in a cochlear implant assembly configured to be implanted within a recipient. The cochlear implant assembly may further include other components, such as an overmold that houses cochlear implant 108 and one or more other components (e.g., an antenna, etc.) of the cochlear implant assembly.

Figure 2:
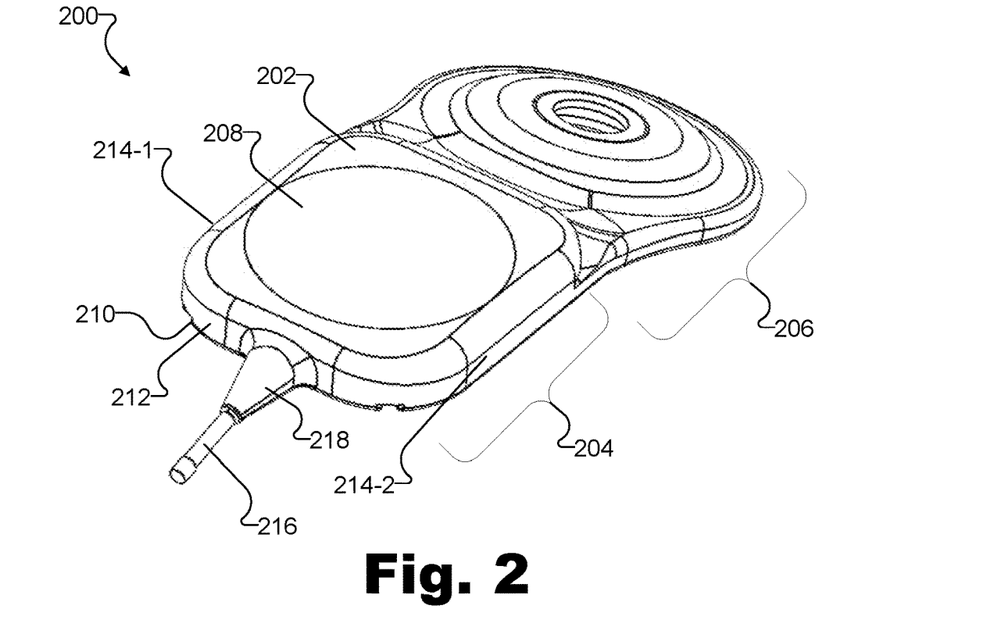
FIGS. 2-3 show an exemplary cochlear implant assembly according to principles described herein.
Figure 3:
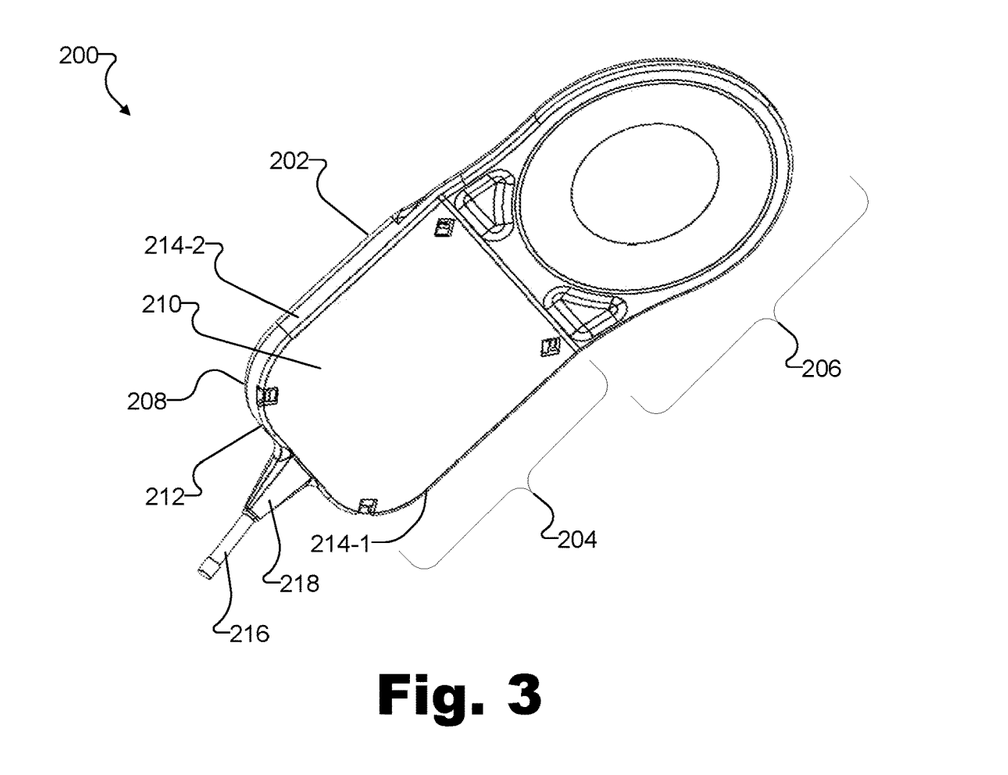

To illustrate, FIG. 2 shows a perspective view of a front side of an exemplary cochlear implant assembly 200 ("assembly 200"), and FIG. 3 shows a perspective view of a back side of assembly 200. As shown in FIGS. 2 and 3, assembly 200 may include an overmold 202 having a first portion 204 and a second portion 206. First portion 204 of overmold 202 may be configured to cover a cochlear implant (e.g., cochlear implant 108) and second portion 206 of overmold 202 may be configured to cover an antenna and/or any other suitable component of assembly 200. In some examples, overmold 202 may be a biocompatible material, such as silicone, overmolded over the internal components. In alternative examples, overmold 202 may be a preformed casing.

As shown, first portion 204 of overmold 202 includes a front surface 208, a back surface 210, an end side surface 212, and lateral side surfaces 214-1 and 214-2. When assembly 200 is implanted in a recipient, front surface 208 may be positioned such that front surface 208 faces outward within the recipient (i.e., away from the skull of the recipient), and back surface 210 may be positioned such that back surface 210 faces inward within the recipient (i.e., towards the skull of the recipient). End side surface 212 and lateral side surfaces 214-1 and 214-2 adjoin front surface 208 and back surface 210. End side surface 212 is located at a longitudinal end of assembly 200 and, when implanted in the recipient, may be positioned closest to the cochlea of the recipient. Cochlear lead 216 may be connected to assembly 200 (i.e., to cochlear implant 108) through overmold 202, and the connection may be protected and secured by fantail 218. In some examples, cochlear lead 216 may be connected to assembly 200 at end side surface 212.

Figure 4:
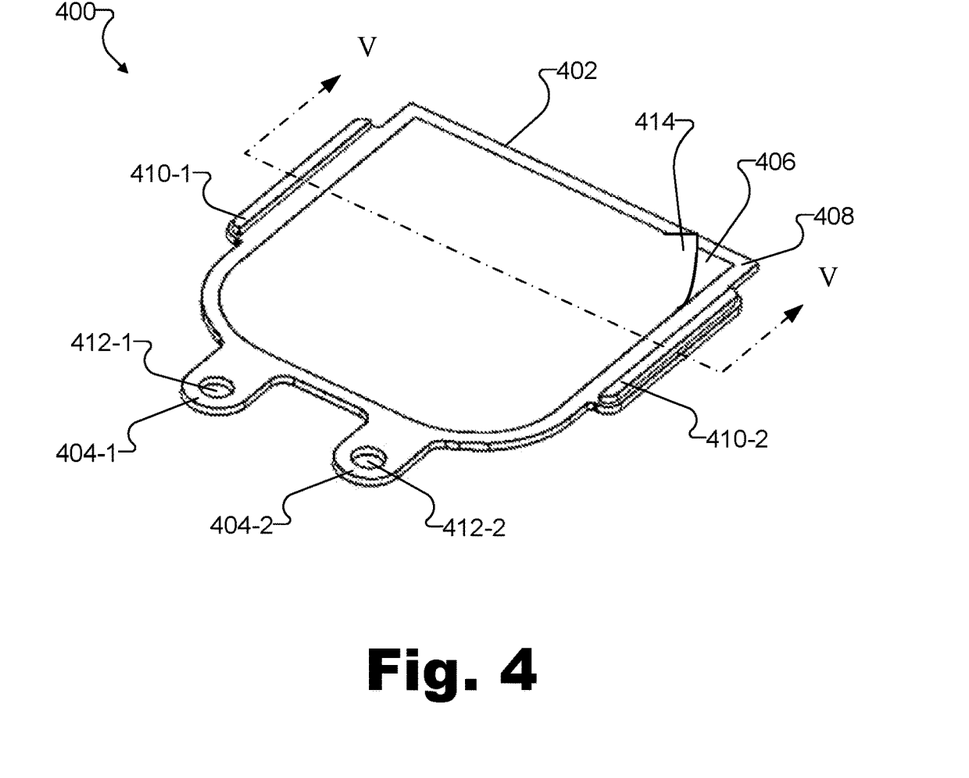
FIG. 4 shows an exemplary fixation device for use with the cochlear implant assembly shown in FIGS. 2-3 according to principles described herein.
Figure 5:
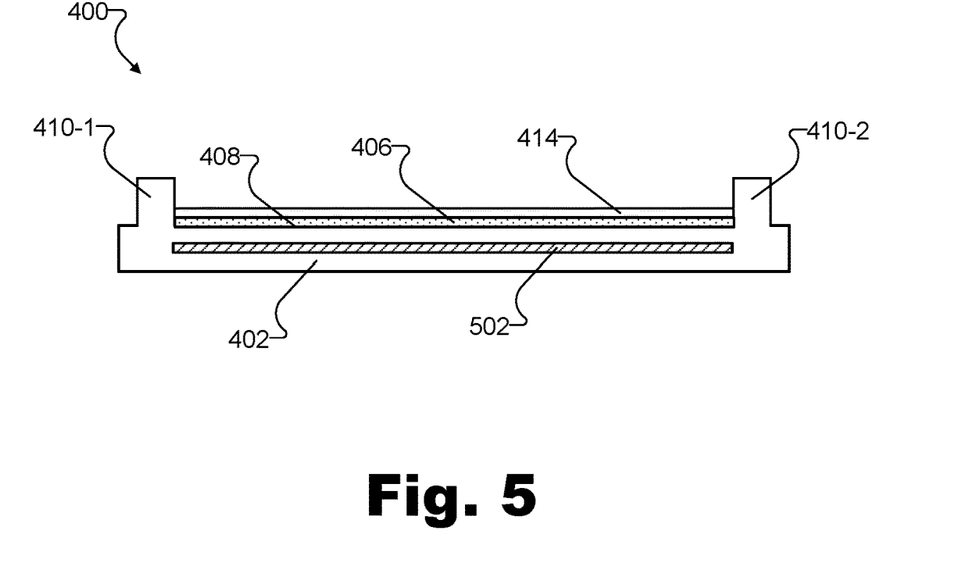
FIG. 5 shows a cross-sectional view of the fixation device shown in FIG. 4 according to principles described herein.

FIG. 4 shows a perspective view of an exemplary fixation device 400 that may be used with assembly 200, and FIG. 5 shows a cross-sectional view of fixation device 400 taken along the V-V line shown in FIG. 4. As shown in FIGS. 4 and 5, fixation device 400 may include a body member 402, anchor members 404 (i.e., anchor members 404-1 and 404-2), and an adhesion element 406.

Body member 402 of fixation device 400 may comprise a unitary body configured to attach to an outer surface (e.g., front surface 208, back surface 210, end side surface 212, and/or a lateral side surface 214) of assembly 200. To this end, body member 402 may include a contact surface 408 shaped to conform to the outer surface of assembly 200 to which fixation device 400 will attach. For example, if fixation device 400 is configured to attach to back surface 210 of assembly 200, contact surface 408 may be shaped to conform to a surface shape of back surface 210. Additionally, adhesion element 406 is provided on contact surface 402, as will be described below in more detail.

In some examples, body member 402 may also include one or more rails to facilitate proper alignment and positioning of fixation device 400 on assembly 200. For instance, body member 402 may include rails 410 (e.g., first rail 410-1 and second rail 410-2), which may be configured to abut against surfaces of assembly 200 (e.g., lateral side surfaces 214) other than the outer surface to which fixation device 400 is attached. Body member 402 may include any number of rails, positioned at any location(s), as may suit a particular implementation.

Body member 402 may be formed of any suitable biocompatible material, such as a polysiloxane (e.g., medical grade silicone rubber). In some examples, body member 402 may be formed of a rigid material (e.g., silicone having a Shore A hardness of approximately 90) to provide strength for securing assembly 200 in place within a recipient's body.

As shown in FIG. 5, body member 402 may include a reinforcing member 502 configured to provide strength to body member 402. As shown, reinforcing member 502 is embedded within body member 402 and, in some examples, may be more rigid than body member 402. For example, reinforcing member 502 may have a Shore A hardness and/or elastic modulus greater than the Shore A hardness and/or elastic modulus of body member 402. Reinforcing member 502 may be formed of any suitable material, including without limitation a metal (e.g., stainless steel, titanium, etc.), plastic (e.g., PEEK, etc.), and the like. Reinforcing member 502 may have a solid planar form or it may have a mesh or other wire-type form. In some examples, body member 402 may be formed by overmolding reinforcing member 502 with an outer covering (e.g., a polysiloxane). In some alternative examples, reinforcing member 502 is not included in body member 402.

Referring again to FIG. 4, anchor members 404 of fixation device 400 are configured for use in securing fixation device 400 to a body of a recipient of assembly 200. Hence, when fixation device 400 is attached to assembly 200, anchor members 404 facilitate securing of assembly 202 within the recipient. As shown, anchor members 404 may be plate-shaped members extending from body member 402 in a plane substantially parallel to contact surface 408. Anchor members 404 may include holes 412 (e.g., first hole 412-1 and second hole 412-2) for securing fixation device 400 to the recipient. In some examples, anchor members 404 may be configured to secure fixation device 400 to the recipient by one or more screws (e.g., one or more bone screws), sutures, staples, or other fasteners configured to pass through holes 412 and secure to bone or tissue within the recipient.

Anchor members 404 may extend from body member 402 in any suitable location. For example, as shown in FIG. 4, anchor members 404 may extend from body member 404 at a position corresponding to end side surface 212. Alternative locations for anchor members 404 will be described herein.

In some examples, anchor members 404 may be formed integrally with body member 402. Anchor members 404 may also include a reinforcing member (not shown) to provide strength at the location where fixation device 400 is secured to the recipient's body. In some examples, the reinforcing member of the anchor members may extend from reinforcing member 502 and may be formed integrally with reinforcing member 502.

Adhesion element 406 of fixation device 400 may be provided on contact surface 408 to enable attachment of fixation device 400 (i.e., body member 402) to the outer surface of assembly 200. Adhesion element 406 may be any suitable element configured to attach body member 402 (i.e., contact surface 408) to the outer surface of assembly 200 by adhesion. Adhesion element 406 may cover all or a portion of contact surface 408. In some examples, a peel-off wrapper 414 (e.g., a paper or plastic film) may be provided over adhesion element 406 to prevent unwanted adhesion of body member 402 to other surfaces. Peel-off wrapper 414 may be removed by a user (e.g., a surgeon) when body member 402 is to be attached to assembly 200.

Figure 6:
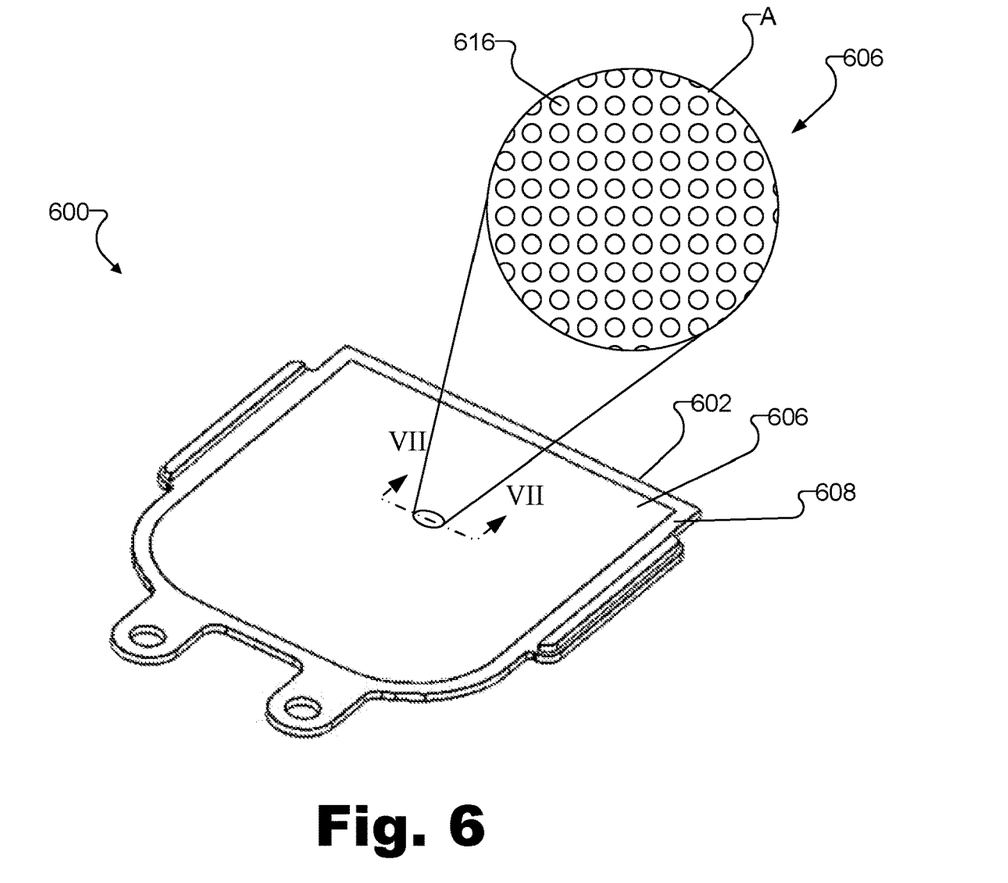
FIG. 6 illustrates an exemplary adhesion element of the fixation device shown in FIG. 4 according to principles described herein.
Figure 7:
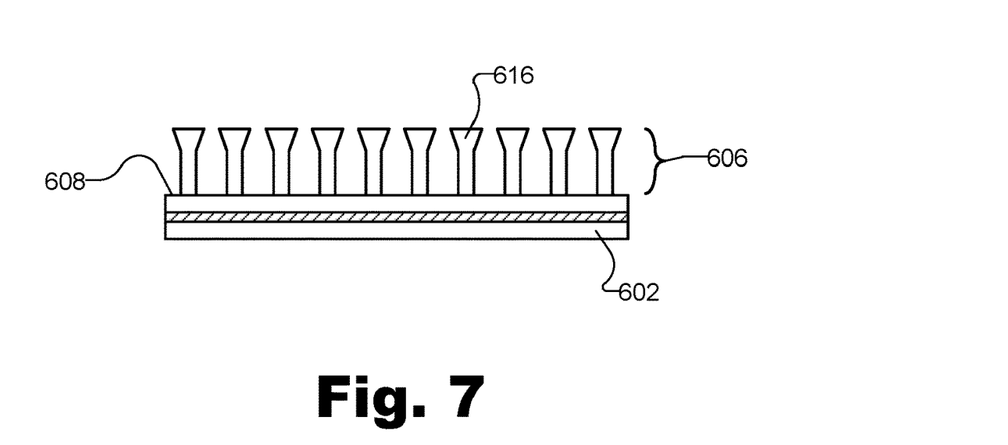
FIG. 7 illustrates a cross-sectional view of the adhesion element of the fixation device shown in FIG. 6 according to principles described herein.

In some examples, adhesion element 406 may be implemented by a gecko adhesive. As used herein, "gecko adhesive" includes any dry adhesive or biomimetic adhesive having synthetic setae that provides adhesion, such as by operation of van der Waals forces. FIG. 6 illustrates an exemplary fixation device 600 having a gecko adhesive. FIG. 7 shows a cross-sectional view of detail area A of FIG. 6. As shown in FIGS. 6 and 7, fixation device 600 includes a body member 602 and a gecko adhesive 606 provided on a contact surface 608 of body member 602. Detail area A of FIG. 6 shows a plan view of a portion of gecko adhesive 606 provided on contact surface 608. As shown in detail area A and FIG. 7, gecko adhesive 606 is constituted by a plurality of gecko fibers 616 that protrude from contact surface 608. Gecko fibers 616 may take any shape and form as may suit a particular implementation. Additionally, gecko fibers 616 may be arranged in any suitable pattern or may be arranged randomly, as may suit a particular implementation. In some examples, gecko adhesive 606 may be formed integrally with body member 602. Alternatively, gecko adhesive 606 may be a tape or other film that is separately formed and/or adhered to contact surface 608.

Gecko adhesive 606 securely attaches fixation device 600 to assembly 200. When fixation device 600 is secured to a recipient's body, gecko adhesive 606 holds assembly 200 in place without device migration while recipient tissue around the implant site heals.

In some examples, gecko adhesive 606 is configured to make fixation device 600 removable from assembly 200. Thus, if a surgeon attaches fixation device 600 to assembly 200 but later decides to not use fixation device 600, the surgeon can remove fixation device 600 and implant only assembly 200 in the recipient.

Referring again to FIGS. 4 and 5, and as mentioned previously, adhesion element 406 may be implemented by any suitable element configured to attach body member 402 (i.e., contact surface 408) to the outer surface of assembly 200 by adhesion. In some examples, adhesion element 406 may be implemented by an adhesive film coated on contact surface 408 of body member 402.

Figure 8:
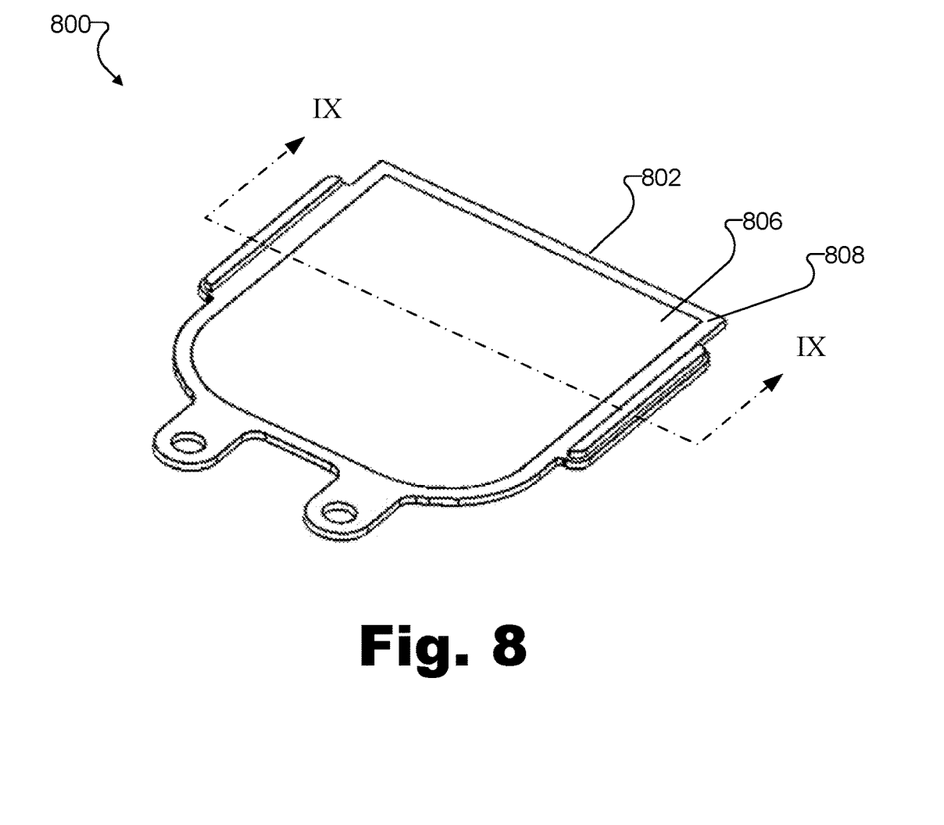
FIG. 8 illustrates another exemplary adhesion element of the fixation device shown in FIG. 4 according to principles described herein.
Figure 9:
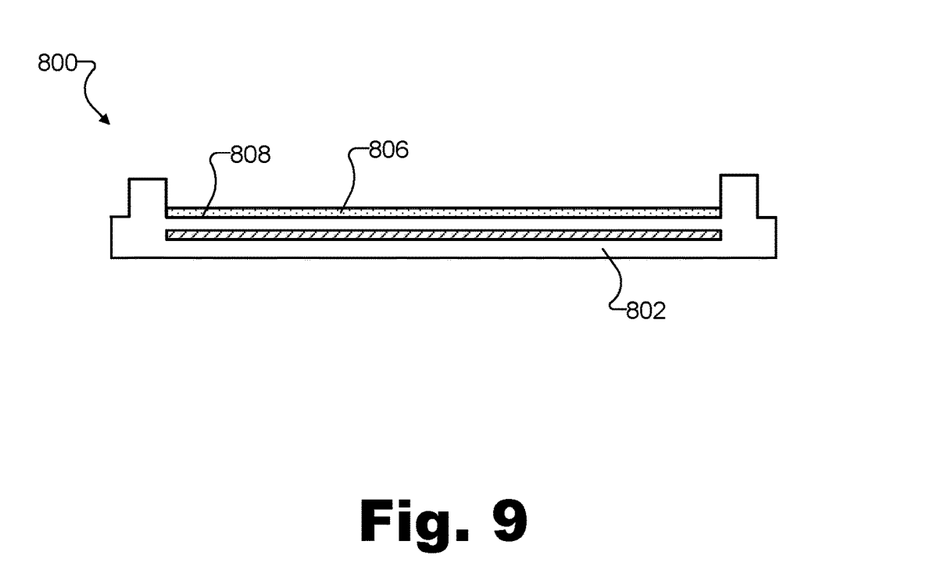
FIG. 9 illustrates a cross-sectional view of the adhesion element of the fixation device shown in FIG. 8 according to principles described herein.

FIG. 8 illustrates an exemplary fixation device 800 in which the adhesion element comprises an adhesive film. FIG. 9 shows a cross-sectional view of fixation device 800 taken along the IX-IX line shown in FIG. 8. As shown in FIGS. 8 and 9, fixation device 800 includes a body member 802 and an adhesive film 806 coated on a contact surface 808 of body member 802. Adhesive film 806 may be any suitable type of adhesive configured to bond body member 802 to an outer surface of assembly 200. For example, if body member 802 and the outer surface of assembly 200 are formed of a silicone, adhesive film 806 may be a silicone adhesive, i.e., an adhesive configured to bond silicone. Suitable adhesives that may be used as adhesive film 818 may include, without limitation, MED-1137P, MED1-1356P, and MED1-4013P, all manufactured by NuSil™ Technology LLC (Carpinteria, Calif.), and SS-67B, manufactured by Silicone Solutions (Cuyahoga Falls, Ohio). In some examples, adhesive film 806 may be configured to be cured by application of pressure, heat, infra-red light radiation, and/or ultraviolet radiation.

Adhesive film 806 securely attaches fixation device 800 to assembly 200. When fixation device 800 is secured to a recipient's body, adhesive film 806 holds assembly 200 in place without device migration while recipient tissue around the implant site heals.

Figure 10A:
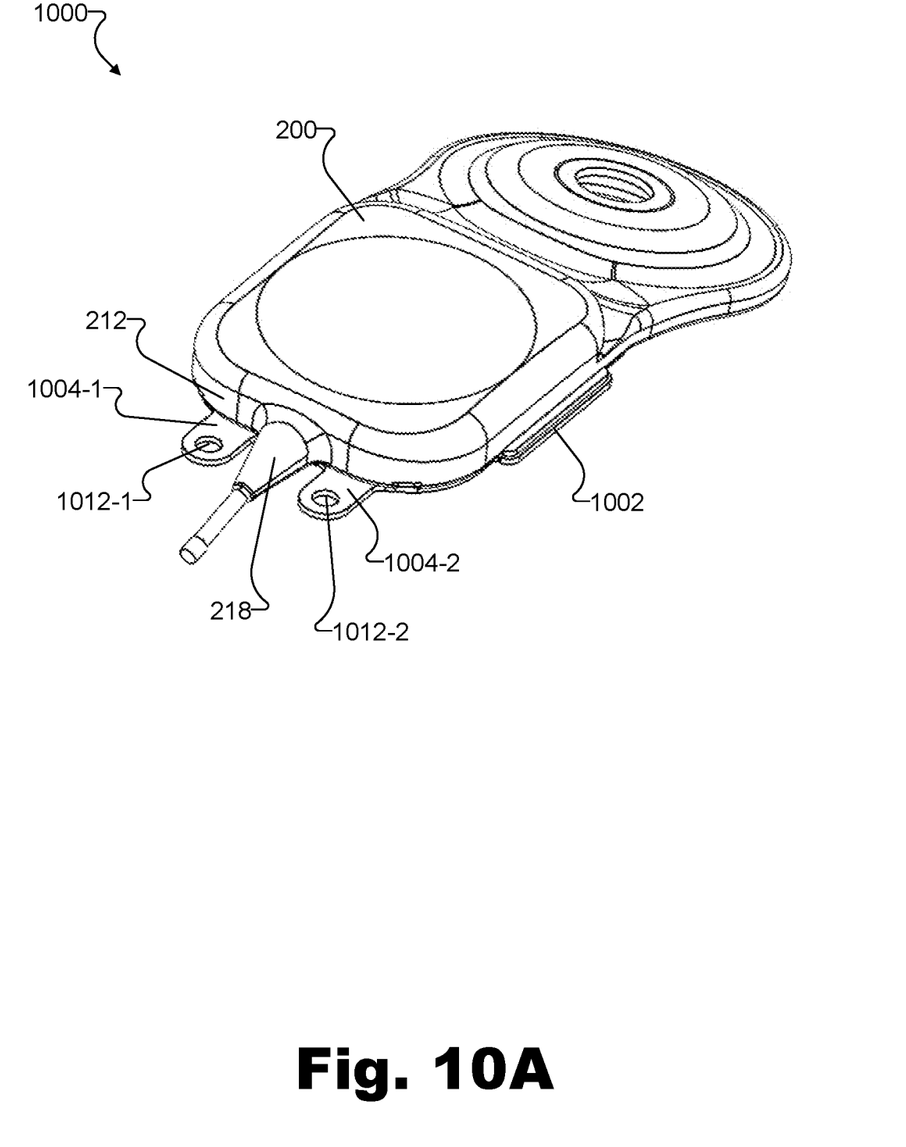
FIG. 10A illustrates an exemplary configuration of the fixation device shown in FIG. 4 attached to the cochlear implant assembly shown in FIGS. 2-3 according to principles described herein.

FIG. 10A illustrates an exemplary configuration 1000 in which a fixation device 1002 (e.g., fixation device 400, fixation device 600, or fixation device 800) is attached to an outer surface (e.g., back surface 210) of assembly 200. Anchor members 1004 (i.e., first anchor member 1004-1 and second anchor member 1004-2) protrude from end side surface 212 on either side of fantail 218. When assembly 1000 is implanted within a recipient's body, assembly 1000 can be secured in a desired position by inserting a fastener (e.g., a bone screw or a suture) through a holes 1012 (e.g., first hole 1012-1 and/or second hole 1012-2) and attaching the fasteners to bone or tissue within the recipient's body.

Figure 10B:
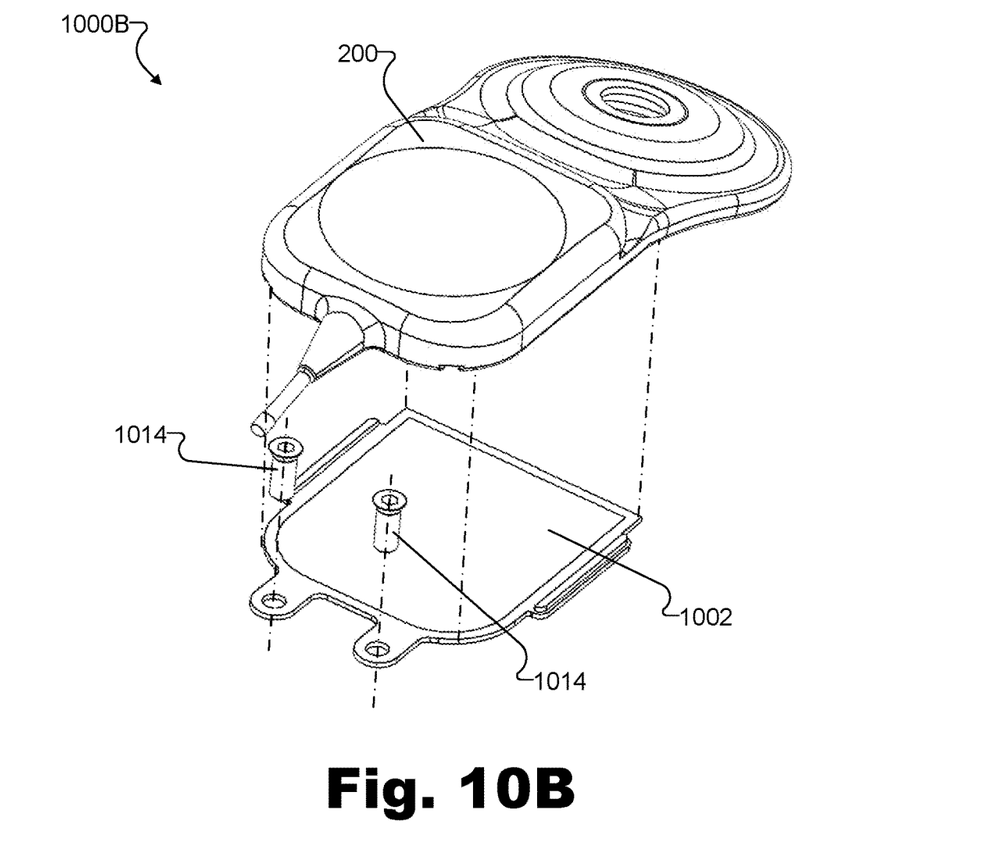
FIG. 10B illustrates an exemplary kit including the fixation device shown in FIG. 4 and the cochlear implant assembly shown in FIGS. 2-3 according to principles described herein.
Figure 10C:
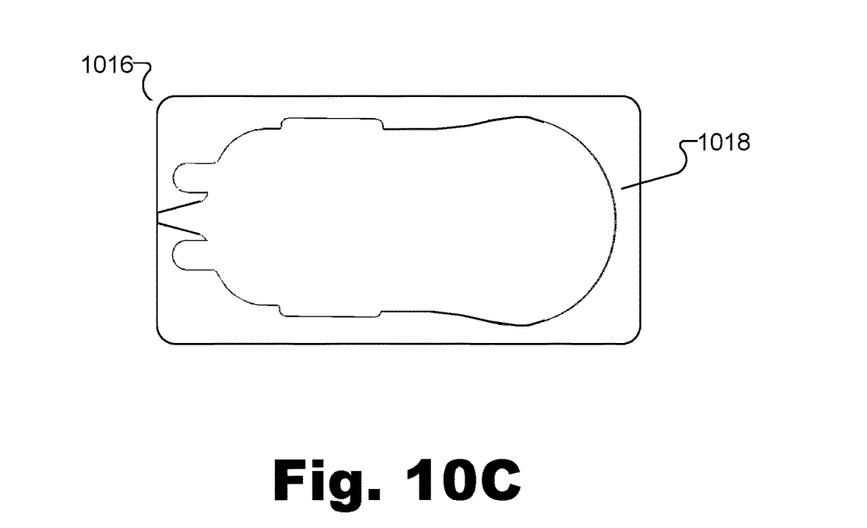
FIG. 10C illustrates a plan view of an exemplary jig that may be provided with the kit shown in FIG. 10B according to principles described herein.

FIG. 10B illustrates an exploded view of an exemplary kit 1000B in which assembly 200 is provided with fixation device 1002 and a set of one or more bone screws 1014. As shown, kit 1000B includes two bone screws 1014, but kit 1000B may include any number of bone screws or other suitable fasteners as may suit a particular implementation (e.g., may include one or more extra bone screws 1014 in the event that a bone screw 1014 is lost). In some examples, kit 1000B may include a jig 1016, as shown in FIG. 10C. Jig 1016 is configured to position fixation device 1002 in the proper position on the outer surface of assembly 200. For example, an inside surface 1018 of jig 1016 may be shaped to conform (like a mold) to the combined shape of fixation device 1002 and assembly 200, thus facilitating and ensuring proper positioning of fixation device 1002 on the outer surface of assembly 200. Kit 1000B may also include any other tools that may aid in the assembly of kit 1000B, such as a screwdriver (not shown) for securing bone screws 1014 within the recipient's body and pliers (not shown) for grasping bone screws 1014.

Figure 11:
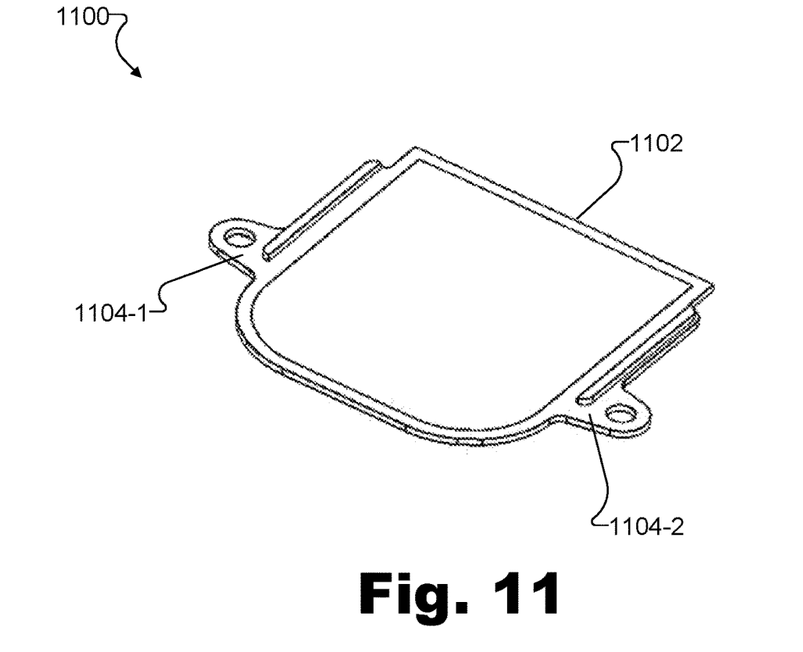
FIG. 11 shows another exemplary fixation device for use with the cochlear implant assembly shown in FIGS. 2-3 according to principles described herein.

An exemplary modification of fixation device 400 is shown in FIG. 11 as fixation device 1100. Fixation device 1100 is substantially similar to fixation device 400 shown in FIG. 4 except that anchor members 1104 (e.g., first anchor member 1104-1 and second anchor member 1104-2) extend from the sides, rather than the end, of body member 1102.

Figure 12:
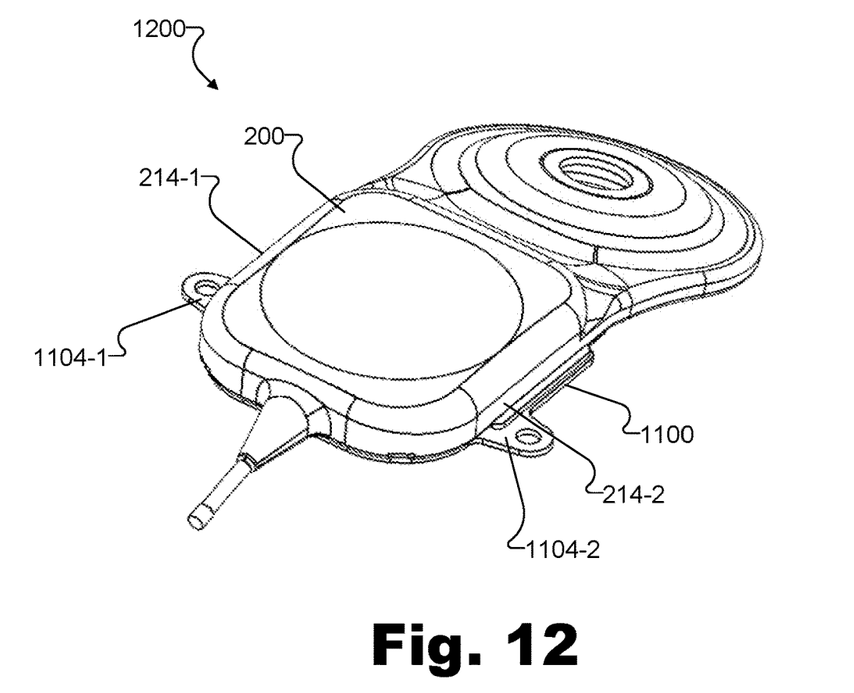
FIG. 12 illustrates an exemplary configuration of the fixation device shown in FIG. 11 attached to the cochlear implant assembly shown in FIGS. 2-3 according to principles described herein.

FIG. 12 illustrates an exemplary configuration 1200 in which fixation device 1100 is attached to an outer surface (e.g., back surface 210) of assembly 200. As shown, anchor members 1104 are positioned to protrude from lateral side surfaces 214-1 and 214-2 of assembly 200.

Figure 13:
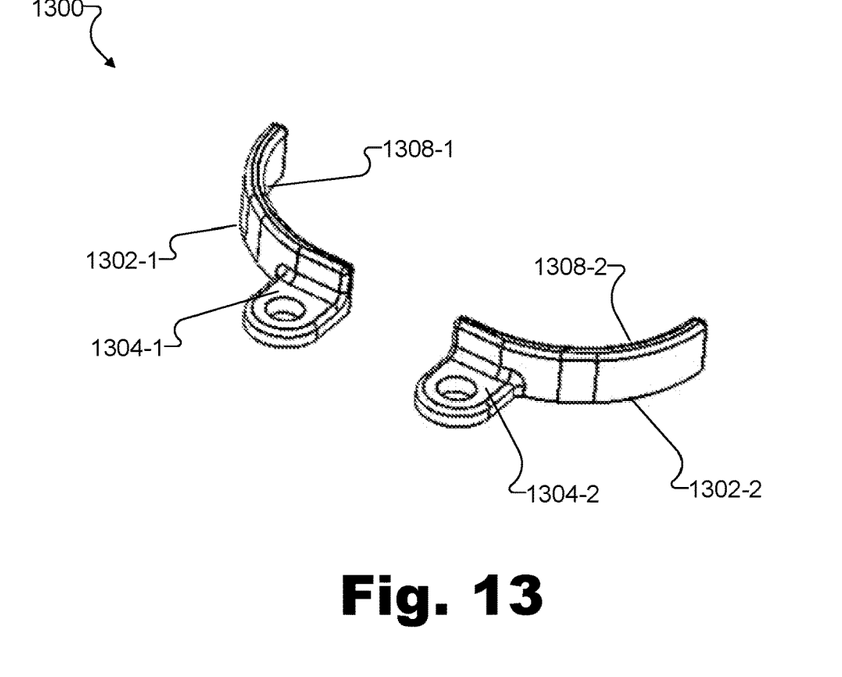
FIG. 13 shows another exemplary fixation device for use with the cochlear implant assembly shown in FIGS. 2-3 according to principles described herein.

Referring now to FIG. 13, another exemplary fixation device 1300 is shown. Fixation device 1300 includes a plurality of body members 1302 (e.g., first body member 1302-1 and second body member 1302-2), a plurality of anchor members 1304 (e.g., first anchor member 1304-1 and second anchor member 1304-2), and a plurality of adhesion elements (not shown) provided on a plurality of contact surfaces 1308 (e.g., first contact surface 1308-1 and second contact surface 1308-2) of body members 1302. The adhesion elements are configured to attach body members 1302 to an outer surface of assembly 200.

Body members 1302 may be shaped to conform to an outer surface of assembly 200, such as an outer surface of assembly 200 extending from end side surface 212 to a lateral side surface 214. Contact surfaces 1308 of body members 1302 may be configured to attach to this outer surface. Since this outer surface is curved (see FIG. 2), body members 1302 are correspondingly curved. In this way, contact surfaces 1308 of body members 1302 are configured to maintain tight contact with the outer surface of assembly 200 when fixation device 1300 is attached to assembly 200.

Because body members 1302 (e.g., contact surfaces 1308) are configured to attach to end side surface 212 and a lateral side surface 214 of assembly 200, anchor members 1304 extend from body members 1302 in a plane substantially orthogonal to contact surfaces 1308, thereby allowing fixation device 1300 to be secured to the recipient's body.

Figure 14:
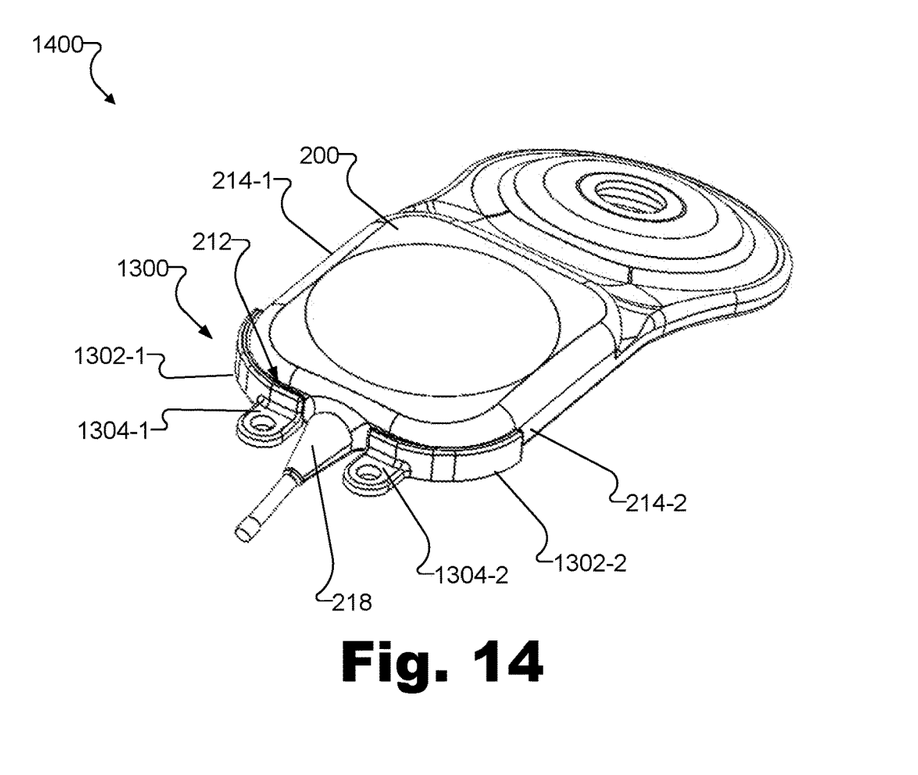
FIG. 14 illustrates an exemplary configuration of the fixation device shown in FIG. 13 attached to the cochlear implant assembly shown in FIGS. 2-3 according to principles described herein.

FIG. 14 illustrates an exemplary configuration 1400 in which fixation device 1300 is attached to an outer surface of assembly 200. As shown, each body member 1302 is attached to an outer surface extending from end side surface 212 to a lateral side surface 214. Anchor members 1304 are positioned to protrude from body members 1302 at end side surface 212 on either side of fantail 218. Because fixation device 1300 attaches only to end side surface 212 and/or lateral side surfaces 214, it does not add any thickness to the profile of assembly 200. Thus, a surgeon need remove very little recipient tissue to accommodate fixation device 1300.

It will be appreciated that fixation device 1300 is not limited to the foregoing configuration, as various modifications may be made as may suit a particular implementation. For example, body members 1302 may be configured to attach only to lateral side surfaces 214, and not to end side surface 212. Additionally or alternatively, anchor members 1304 may be configured to extend from body members 1302 at any location as may suit a particular implementation. Additionally or alternatively, fixation device 1300 is not limited to two anchor members 1304, but may include only one anchor member, or it may include more than two anchor members 1304. Furthermore, fixation device 1300 may include only one body member 1302, or it may include more than two body members.

Figure 15:
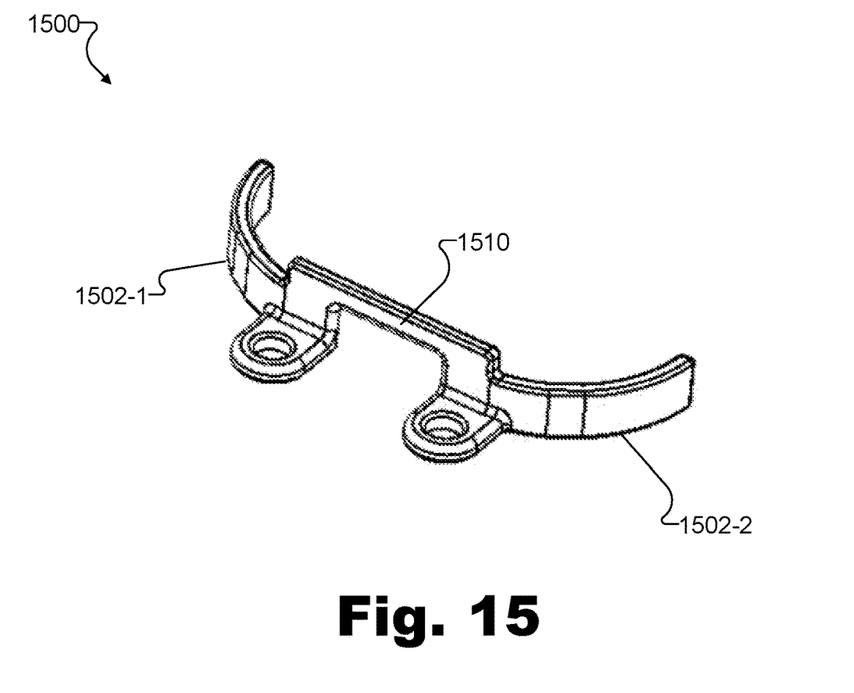
FIG. 15 shows another exemplary fixation device for use with the cochlear implant assembly shown in FIGS. 2-3 according to principles described herein.

Another exemplary modification of fixation device 1300 is shown in FIG. 15 as exemplary fixation device 1500. Fixation device 1500 is substantially similar to fixation device 1300 shown in FIG. 13, except that fixation device 1500 includes bridge 1510 that connects body members 1502 (e.g., first body member 1502-1 and second body member 1502-2). Bridge 1510 maintains the position of body members 1502 relative to one another, thereby facilitating proper alignment and attachment of fixation device 1500 to assembly 200 (see FIG. 16).

Figure 16:
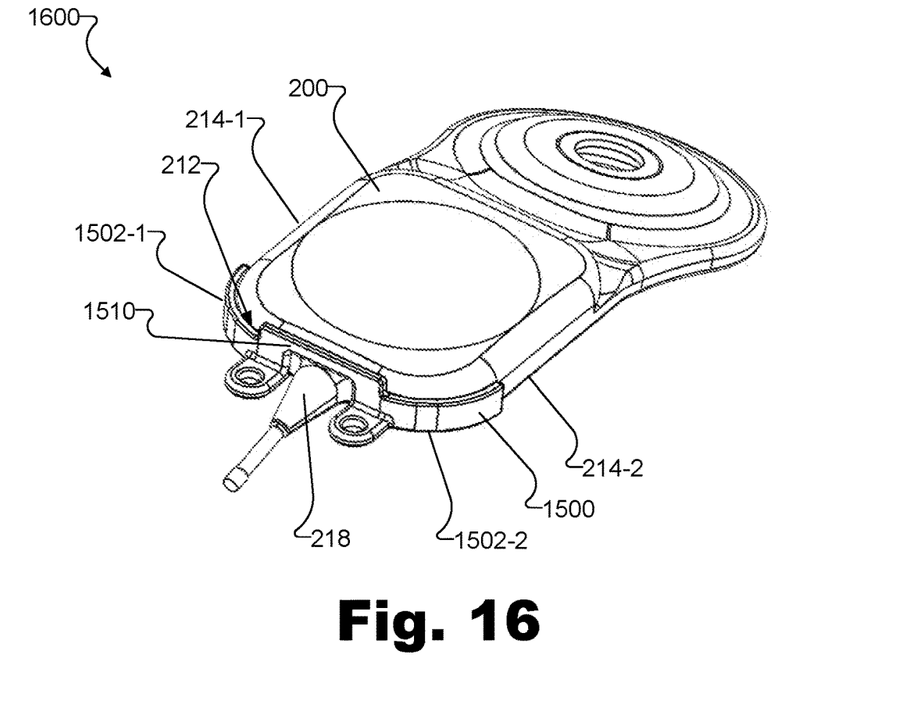
FIG. 16 illustrates an exemplary configuration of the fixation device shown in FIG. 15 attached to the cochlear implant assembly shown in FIGS. 2-3 according to principles described herein.

FIG. 16 shows an exemplary configuration 1600 in which fixation device 1500 is attached to an outer surface of assembly 200. As shown, each body member 1502 is attached to an outer surface extending from end side surface 212 to a lateral side surface 214 on either side of fantail 218. Bridge 1510 is positioned on end side surface 212 above fantail 218.

Bridge 1510 is not limited to the configuration depicted in FIGS. 15 and 16. For example, bridge 1510 may additionally or alternatively be positioned below fantail 218 when fixation device 1500 is attached to assembly 200. Additionally or alternatively, bridge 1510 may extend over one or more other surfaces of assembly 200 (e.g., front surface 208 and/or back surface 210). In some examples, an adhesion element may also be provided on a contact surface of bridge 1510 to strengthen the attachment of fixation device 1500 to assembly 200.

Figure 17:
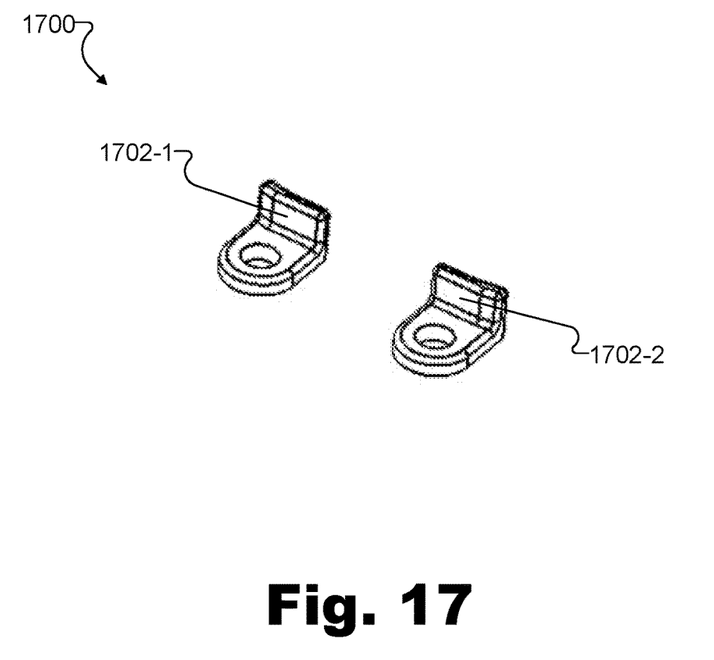
FIG. 17 shows another exemplary fixation device for use with the cochlear implant assembly shown in FIGS. 2-3 according to principles described herein.

Another exemplary modification of fixation device 1300 is depicted in FIG. 17 as exemplary fixation device 1700. Fixation device 1700 is substantially similar to fixation device 1300 shown in FIG. 13, except that body members 1702 (e.g., first body member 1702-1 and second body member 1702-2) of fixation device 1700 are smaller such that they are each configured to attach to one outer surface of assembly 200 (e.g., end side surface 212 or a lateral side surface 214). Fixation device 1700 can be attached to any surface of assembly 200, and at any location, as may suit a particular implementation.

Figure 18:
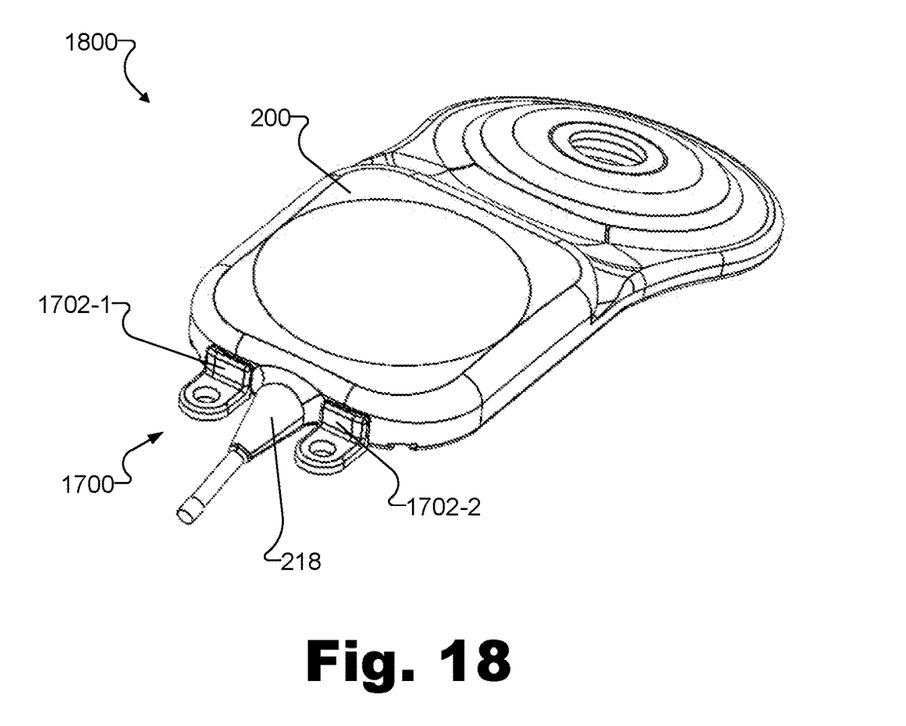
FIG. 18 illustrates an exemplary configuration of the fixation device shown in FIG. 17 attached to the cochlear implant assembly shown in FIGS. 2-3 according to principles described herein.

FIG. 18 illustrates an exemplary configuration 1800 in which fixation device 1700 is attached to an outer surface of assembly 200. As shown, each body member 1702 is attached to end side surface 212 on either side of fantail 218. Because body members 1702 each attach to only one outer surface of assembly 200, fixation device 1700 occupies very little extra space within the recipient.

Figure 19:
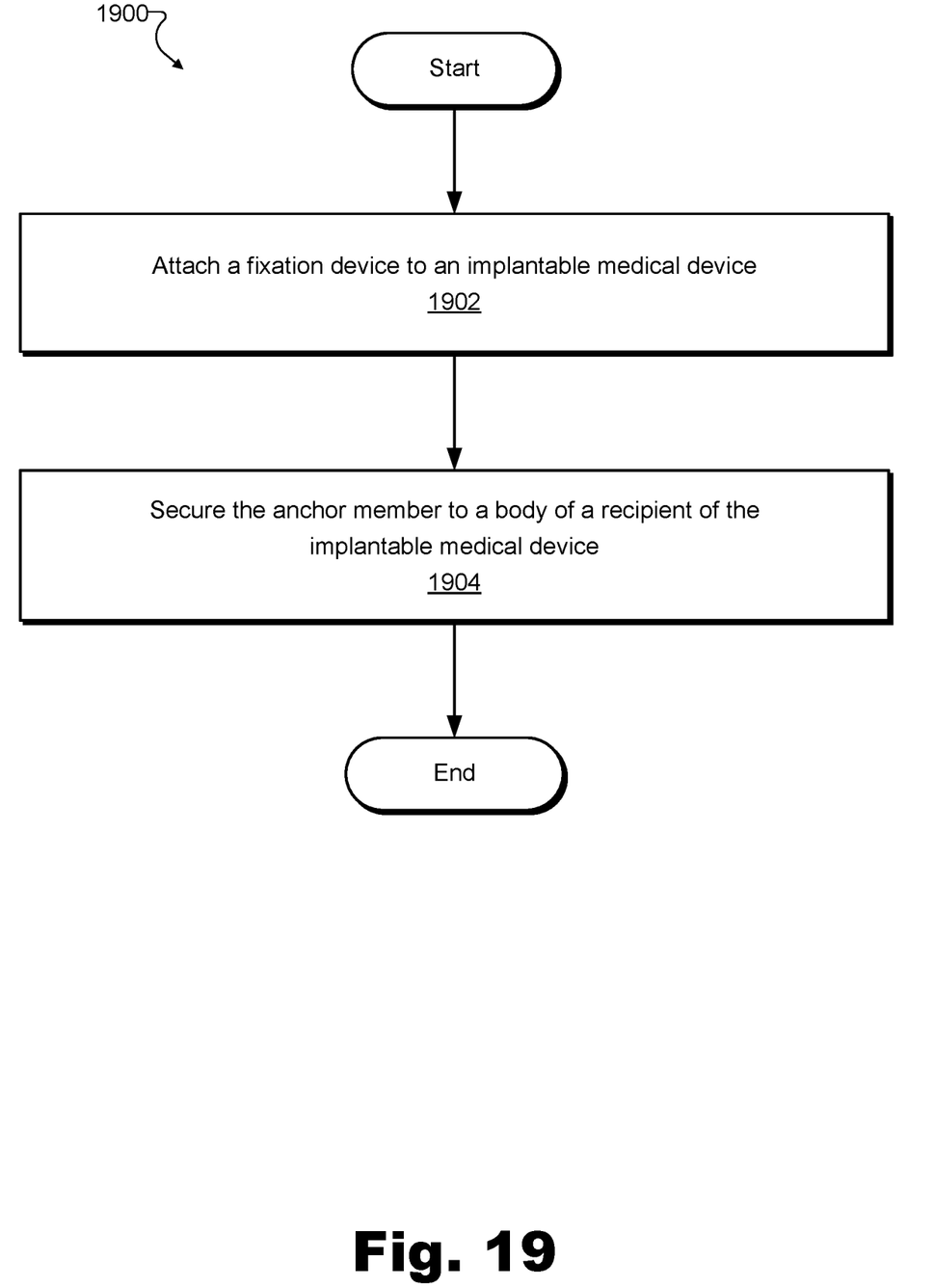
FIG. 19 illustrates an exemplary method according to principles described herein.

FIG. 19 illustrates an exemplary method 1900 for use of a fixation device with an implantable medical device. While FIG. 19 illustrates exemplary operations according to one embodiment, other embodiments may omit, add to, reorder, and/or modify any of the operations shown in FIG. 19.

In operation 1902, a fixation device is attached to an implantable medical device. The fixation device may include a body member comprising a contact surface shaped to conform to an outer surface of the implantable medical device, an adhesion element provided on a contact surface of the body member and configured to attach the body member to the outer surface of the implantable medical device, and an anchor member extending from the body member and having a hole for securing the fixation device to a recipient's body while the body member is attached to the outer surface of the implantable medical device. In some examples, the fixation device may be attached to the implantable medical device by attaching, by the adhesion element, the body member to the outer surface of the implantable medical device. Operation 1902 may be performed in any of the ways described herein.

In operation 1904, the anchor member is secured to the recipient's body. Operation 1904 may be performed in any of the ways described herein.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A fixation device for use with an implantable medical device, the fixation device comprising:
   a body member comprising a contact surface shaped to conform to an outer surface of the implantable medical device;
   an adhesion element provided on a contact surface of the body member and configured to attach the body member to the outer surface of the implantable medical device; and
   an anchor member extending from the body member and having a hole for securing the fixation device within a recipient of the implantable medical device while the body member is attached to the outer surface of the implantable medical device.

2. The fixation device of claim 1, wherein the adhesion element comprises a gecko adhesive.

3. The fixation device of claim 2, wherein the gecko adhesive is formed integrally with the body member.

4. The fixation device of claim 1, wherein the adhesion element comprises an adhesive film coated on the contact surface of the body member.

5. The fixation device of claim 4, wherein the adhesive film comprises a silicone adhesive.

6. The fixation device of claim 1, wherein the adhesion element is configured to removably attach the body member to the outer surface of the implantable medical device.

7. The fixation device of claim 1, wherein the body member is configured to attach to the outer surface of the implantable medical device without a snap-fit attachment.

8. The fixation device of claim 1, wherein
the body member includes a first reinforcing member overmolded with a covering, and
the contact surface of the body member is a surface of the covering.

9. The fixation device of claim 8, wherein
the anchor member includes a second reinforcing member, and
the second reinforcing member extends from the first reinforcing member and is formed integrally with the first reinforcing member.

10. The fixation device of claim 1, wherein the anchor member is configured to secure the fixation device within the recipient by at least one of a screw configured to pass through the hole, a staple configured to pass through the hole, and a suture configured to pass through the hole.

11. A kit comprising:
the fixation device of claim 1,
the implantable medical device, and
a fastener configured to pass through the hole of the anchor member of the fixation device and secure the fixation device within the recipient.

12. The kit of claim 11, further comprising a jig configured to position the fixation device on the outer surface of the implantable medical device.

13. A system comprising:
a cochlear implant assembly comprising:
a cochlear implant, and
an overmold covering the cochlear implant and having an outer surface; and
a fixation device comprising:
a body member comprising a contact surface shaped to conform to the outer surface of the cochlear implant assembly,
an adhesion element provided on the contact surface of the body member and configured to attach the body member to the outer surface of the cochlear implant assembly, and
an anchor member extending from the body member and having a hole for securing the fixation device to a body of a recipient of the cochlear implant assembly while the body member is attached to the outer surface of the cochlear implant assembly.

14. The cochlear implant system of claim 13, wherein the adhesion element comprises a gecko adhesive or an adhesive film coated on the contact surface of the body member.

15. The fixation device of claim 14, wherein the gecko adhesive is formed integrally with the body member.

16. The fixation device of claim 14, wherein the adhesive film comprises a silicone adhesive.

17. The cochlear implant system of claim 13, further comprising a peel-off wrapper covering the adhesion element.

18. The cochlear implant system of claim 13, wherein
the cochlear implant assembly further comprises a cochlear lead connected to the cochlear implant assembly at a side surface of the overmold, and
the outer surface of the cochlear implant assembly is substantially orthogonal to the side surface of the cochlear implant assembly.

19. The cochlear implant system of claim 13, wherein
the cochlear implant assembly further comprises a cochlear lead connected to the cochlear implant assembly at a side surface of the overmold, and
the outer surface of the cochlear implant assembly is the side surface of the cochlear implant assembly.

20. A method comprising:
attaching a fixation device to an implantable medical device, the fixation device comprising:
a body member comprising a contact surface shaped to conform to an outer surface of the implantable medical device,
an adhesion element provided on a contact surface of the body member and configured to attach the body member to the outer surface of the implantable medical device, and
an anchor member extending from the body member and having a hole for securing the fixation device to a body of a recipient of the implantable medical device while the body member is attached to the outer surface of the implantable medical device; and
securing the anchor member to the human body,
wherein the attaching of the fixation device to the implantable medical device comprises attaching, by the adhesion element, the body member to the outer surface of the implantable medical device.

* * * * *